(12) United States Patent
Yoshino et al.

(10) Patent No.: US 10,253,408 B2
(45) Date of Patent: Apr. 9, 2019

(54) COMPOUND, THIN FILM-FORMING MATERIAL, AND THIN FILM MANUFACTURING METHOD

(71) Applicant: ADEKA CORPORATION, Tokyo (JP)

(72) Inventors: Tomoharu Yoshino, Tokyo (JP); Masaki Enzu, Tokyo (JP); Akihiro Nishida, Tokyo (JP); Nana Sugiura, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 3 days.

(21) Appl. No.: 15/559,127

(22) PCT Filed: May 17, 2016

(86) PCT No.: PCT/JP2016/064573
§ 371 (c)(1),
(2) Date: Sep. 18, 2017

(87) PCT Pub. No.: WO2016/203887
PCT Pub. Date: Dec. 22, 2016

(65) Prior Publication Data
US 2018/0051372 A1  Feb. 22, 2018

(30) Foreign Application Priority Data
Jun. 17, 2015  (JP) ................................ 2015-121840

(51) Int. Cl.
| C07F 13/00 | (2006.01) |
| C07F 15/04 | (2006.01) |
| C07F 15/06 | (2006.01) |
| C23C 16/18 | (2006.01) |
| H01L 21/285 | (2006.01) |

(52) U.S. Cl.
CPC .............. *C23C 16/18* (2013.01); *C07F 13/00* (2013.01); *C07F 15/04* (2013.01); *C07F 15/06* (2013.01); *H01L 21/285* (2013.01)

(58) Field of Classification Search
CPC .......... C07F 13/00; C07F 15/04; C07F 15/06
See application file for complete search history.

(56) References Cited

U.S. PATENT DOCUMENTS

| 2013/0164456 A1 | 6/2013 | Winter et al. |
| 2013/0251903 A1* | 9/2013 | Han .................. C23C 16/18 427/252 |
| 2015/0105573 A1 | 4/2015 | Romero |

FOREIGN PATENT DOCUMENTS

| JP | 2013-545755 | 12/2013 |
| WO | 2012/176989 | 12/2012 |

OTHER PUBLICATIONS

International Search Report dated Aug. 16, 2016 in International (PCT) Application No. PCT/JP2016/064573.

* cited by examiner

*Primary Examiner* — Joseph R Kosack
(74) *Attorney, Agent, or Firm* — Wenderoth, Lind & Ponack, L.L.P.

(57) ABSTRACT

A novel compound represented by the general formula (I) or (II) below:

[Chemical Formula 1]

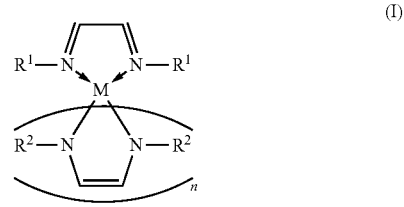

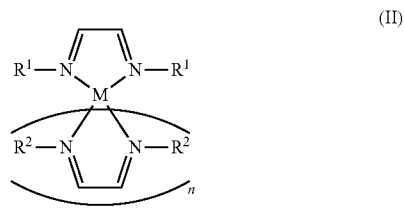

[in the formula, each of $R^1$ and $R^2$ independently represent a $C_{1~12}$ hydrocarbon group, and $Si(R^3)_3$ is optionally substituted for a hydrogen atom in the hydrocarbon group; however, $R^1$ and $R^2$ are different groups; $R^3$ represents a methyl or ethyl group; M represents a metal atom or silicon atom; and n is an integer from 1 to 4].

10 Claims, 4 Drawing Sheets

COMPOUND, THIN FILM-FORMING MATERIAL, AND THIN FILM MANUFACTURING METHOD

TECHNICAL FIELD

The present invention relates to a novel compound, to a thin film-forming material containing the compound, and to a method for manufacturing a thin film using the thin film-forming material, more specifically, to a novel compound consisting of a diazadiene metal compound, to a thin film-forming material containing the compound, and to a method for manufacturing a thin film using the thin film-forming material.

BACKGROUND ART

Thin film materials containing metal elements are used in a variety of applications because of their electrical characteristics, optical characteristics and the like. For example, copper and copper-containing thin films are used as LSI wiring materials because of their strong electrical conductivity, good electromigration resistance and high melting points. Nickel and nickel-containing thin films are used mainly for electronic components such as low resistance films and barrier films, for recording media components such as magnetic films, and for thin film solar cell components such as electrodes. Cobalt and cobalt-containing thin films are used for electrode films, low resistance films, adhesive films, magnetic tapes, ultrahard tool components and the like.

Methods for forming these thin films include sputtering methods, ion plating methods, MOD methods such as coating thermal decomposition and sol-gel methods, and chemical vapor deposition and the like, but chemical vapor deposition (sometimes called "CVD") methods including ALD (Atomic Layer Deposition) methods are the most suitable manufacturing processes because they offer such advantages as compositional controllability, excellent step coverage, applicability to mass production and the possibility of hybrid integration.

A variety of materials have been reported as metal sources for use in chemical vapor deposition. For example, Patent Document 1 discloses a diazadienyl complex that can be used as a material for thin film formation by an ALD method. Patent Document 2 describes a diazadiene metal compound that can be used in chemical deposition or atomic layer deposition. However, neither Patent Document 1 nor 2 discloses a novel compound consisting of the diazadiene metal compound of the present invention.

PRIOR ART DOCUMENTS

Patent Documents

[Patent Document 1] U.S. Patent No. 2013/0164456A1
[Patent Document 2] Patent Laid-Open No. 2013-545755

SUMMARY OF THE INVENTION

Problem to be Solved by the Invention

When vaporizing a material for chemical vapor deposition or the like to form a thin film containing a metal on the surface of a substrate, a thin film-forming material with a high vapor pressure and a low melting point capable of producing a high-quality metal-containing thin film with low energy is desired, but conventional thin film-forming materials have not exhibited these characteristics.

Accordingly, an object of the present invention is to provide a novel compound consisting of a diazadiene metal compound for use in a thin film-forming material with a high vapor pressure and a low melting point capable of producing a high-quality metal-containing thin film with low energy when vaporizing a material for chemical vapor deposition or the like to form a thin film containing a metal on the surface of a substrate, together with a thin film-forming material containing this compound and a method for manufacturing a thin film using this thin film-forming material.

Means for Solving the Problem

The inventors arrived at the present invention as a result of earnest research aimed at solving these problems upon discovering that the problems could be solved with a specific compound.

That is, the present invention provides a novel compound represented by the general formula (I) or general formula (II) below, a thin film-forming material containing the compound and a method for manufacturing a thin film using this material:

[Chemical Formula 1]

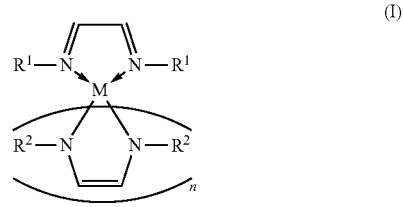

(I)

[In the formula, each of $R^1$ and $R^2$ independently represent a $C_{1\sim12}$ hydrocarbon group, and $Si(R^3)_3$ is optionally substituted for a hydrogen atom in the hydrocarbon group. However, $R^1$ and $R^2$ are different groups. $R^3$ represents a methyl or ethyl group, M represents a metal atom or silicon atom, and n is an integer from 1 to 4.]

[Chemical Formula 2]

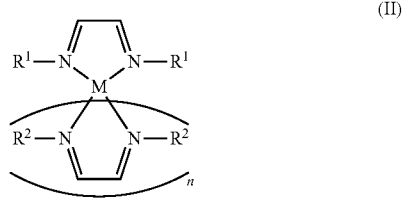

(II)

[In the formula, $R^1$, $R^2$, $R^3$, M and n are as in the general formula (I).]

Effects of the Invention

With the present invention, it is possible to obtain a compound with a high vapor pressure and a low thermal decomposition temperature that has a low melting point and becomes liquid at normal pressure, 30° C. or when heated slightly. This compound is especially suited as a thin film-forming material for forming a metal thin film by a CVD method, and can be used by preference as a thin film-forming material for forming a metal thin film by an ALD method in particular.

BEST MODE FOR CARRYING OUT THE INVENTION

Figure 1:
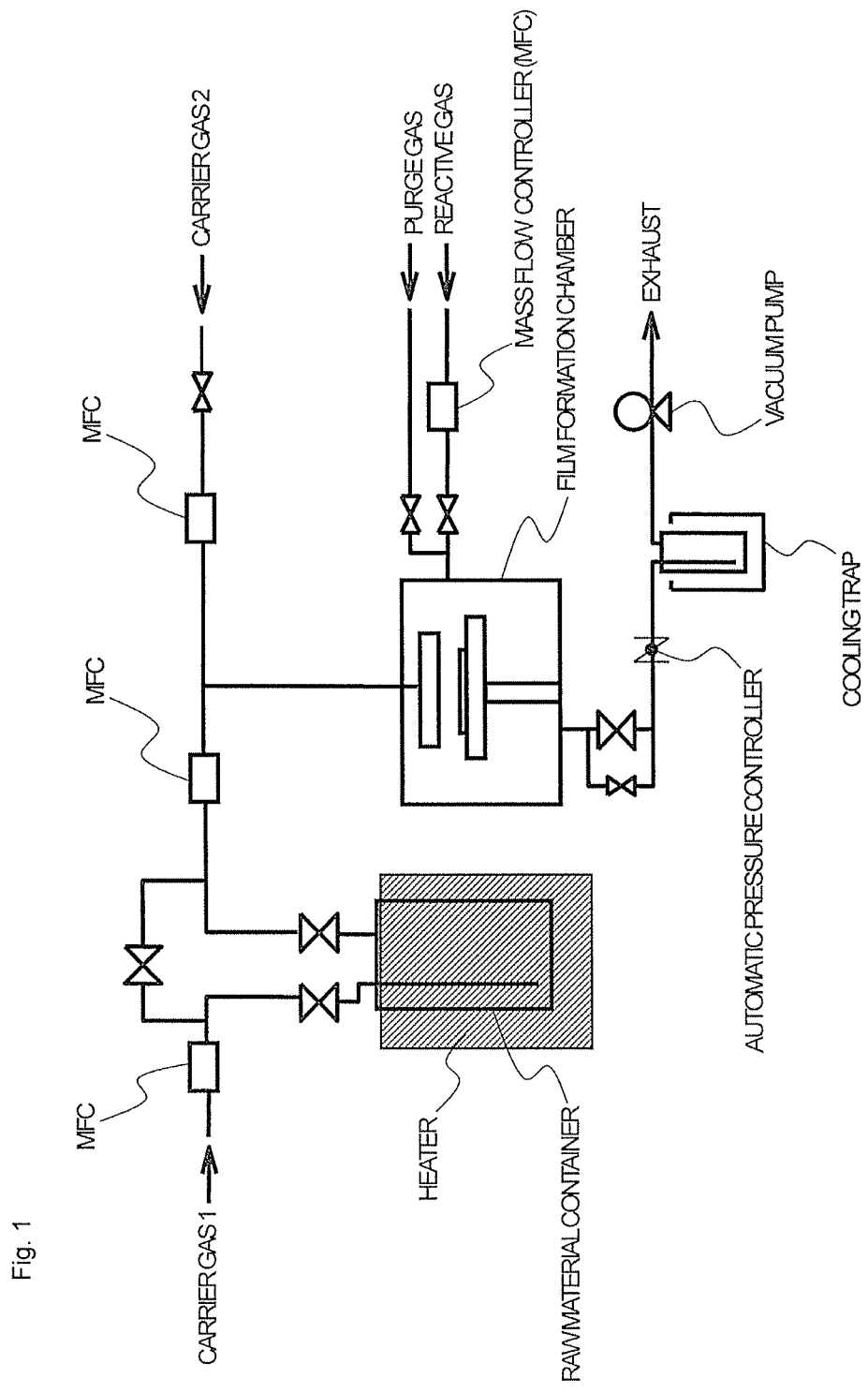
FIG. 1 is an outline drawing showing one embodiment of a chemical vapor deposition apparatus that can be used in the thin film manufacturing method of the present invention.

The compound of the invention is represented by the general formula (I) or general formula (II) above, is suitable as a precursor in a thin film manufacturing method such as a CVD method or the like having a vaporization step, and can also form a thin film by an ALD method. The compound of the present invention has a low melting point, and becomes liquid at normal pressure, 30° C. or when heated slightly. Since compounds with low melting points have good transport properties, they are suitable as precursors in thin film manufacturing methods such as CVD methods or the like that include vaporization steps. Moreover, the compound of the present invention also has a low thermal decomposition temperature. A compound with a low thermal decomposition temperature can yield a thin film with low energy when used as a precursor in a thin film manufacturing method such as a CVD method or the like that includes a vaporization step.

In the general formula (I) and general formula (II) above of the present invention, each of $R^1$ and $R^2$ independently represent a $C_{1\sim10}$ hydrocarbon group, and $Si(R^3)_3$ is optionally substituted for a hydrogen atom in the hydrocarbon group. However, $R^1$ and $R^2$ are different groups. $R^3$ represents a methyl or ethyl group, M represents a metal atom or silicon atom, and n is an integer from 1 to 4.

Examples of the $C_{1\sim12}$ hydrocarbon groups represented by $R^1$ and $R^2$ include alkyl, alkenyl, cycloalkyl, aryl and cyclopentadienyl groups and the like. $Si(R^3)_3$ is optionally substituted for hydrogen atoms in these hydrocarbon groups. $Si(R^3)_3$ represents a trimethylsilyl group or triethylsilyl group, and the number of $Si(R^3)_3$ groups substituted for hydrogen atoms is preferably one per hydrocarbon group.

Examples of the alkyl include methyl, ethyl, propyl, isopropyl, butyl, isobutyl, sec-butyl, tert-butyl, pentyl, amyl, isoamyl, hexyl, heptyl, isoheptyl, octyl, isooctyl, 2-ethylhexyl, nonyl, isononyl, decyl, dodecyl and the like.

Examples of the alkenyl include vinyl, 1-methylethenyl, 2-methylethenyl, propenyl, butenyl, isobutenyl, pentenyl, hexenyl, heptenyl, octenyl, decenyl and the like.

Examples of the cycloalkyl include cyclohexyl, cyclopentyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, methylcycloheptenyl and the like.

Examples of the aryl include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tertiary butylphenyl, 4-hexylphenyl, 4-cyclohexylphenyl and the like.

Examples of the cyclopentadienyl include cyclopentadienyl, methyl cyclopentadienyl, ethyl cyclopentadienyl, propyl cyclopentadienyl, isopropyl cyclopentadienyl, butyl cyclopentadienyl, sec-butyl cyclopentadienyl, isobutyl cyclopentadienyl, tert-butyl cyclopentadienyl, dimethyl cyclopentadienyl, tetramethyl cyclopentadienyl and the like.

In the general formula (I) or general formula (II) above, M represents a metal atom or silicon atom. The metal atom is not particularly limited, but examples include lithium, sodium, potassium, magnesium, calcium, strontium, barium, radium, scandium, yttrium, titanium, zirconium, hafnium, vanadium, niobium, tantalum, chromium, molybdenum, tungsten, manganese, iron, osmium, cobalt, rhodium, iridium, nickel, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium. Of these copper, iron, nickel, cobalt, and manganese are especially desirable as M because they can yield a good quality thin film with low energy when manufacturing a thin film by an ALD method or the like.

In the general formula (I) or general formula (II) above, n represents an integer from 1 to 4. Preferably n is 1.

In the general formula (I) or general formula (II) above, it is desirable if $R^1$ is a $C_{1\sim5}$ primary alkyl group and $R^2$ is a $C_{1\sim5}$ secondary or tertiary alkyl group because this produces a high vapor pressure, a low melting point and a low thermal decomposition temperature. However, a compound in which $R^1$ and $R^2$ are $C_{1\sim5}$ secondary or tertiary alkyl groups has greater storage stability at high temperatures than a compound in which $R^1$ is a primary alkyl group and $R^2$ is a secondary or tertiary alkyl group. In particular, a compound in which $R^1$ is a secondary alkyl group and $R^2$ is a tertiary alkyl group is desirable because it has especially high vapor pressure and low thermal stability. These effects are particularly great in a compound in which $R^1$ is an isopropyl group and $R^2$ is a tert-butyl group, which is also especially desirable because it does not deteriorate over the course of 3 weeks or more even when left at normal pressure at 120° C. Moreover, if M is copper, iron, nickel, cobalt or manganese, n is especially desirable as 1 because then the effects of high vapor pressure, low melting point and low thermal decomposition temperature are especially strong in this case.

In methods for manufacturing thin films by MOD methods without a vaporization step, $R^1$ and $R^2$ may be selected at will according to the solubility in the solvent used, the nature of the thin film forming reaction and the like.

Preferred specific examples of the compound represented by the general formula (I) include the compounds represented by chemical formulas No. 1 to No. 9 below, in which M is cobalt. In the chemical formulas No. 1 to No. 9, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 3]

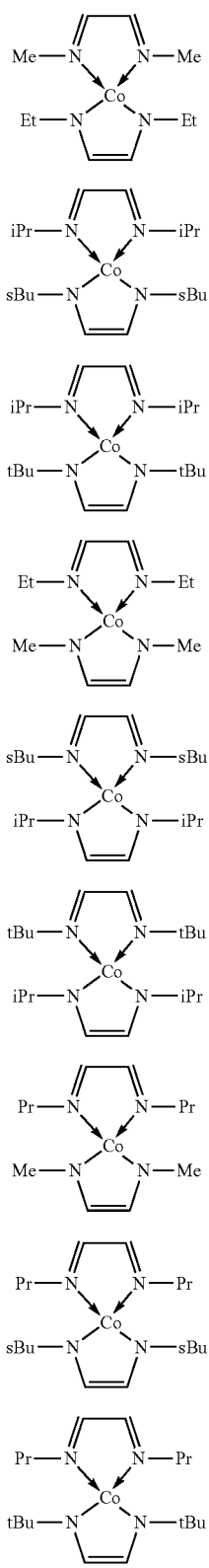

Compound No. 1
Compound No. 2
Compound No. 3
Compound No. 4
Compound No. 5
Compound No. 6
Compound No. 7
Compound No. 8
Compound No. 9

Preferred specific examples of the compound represented by the general formula (I) also include the compounds represented by chemical formulas No. 10 to No. 18 below, in which M is copper. In the chemical formulas No. 10 to No. 18, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 4]

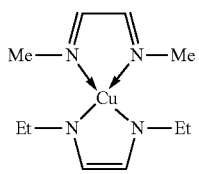

Compound No. 10

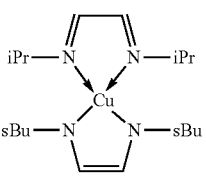

Compound No. 11

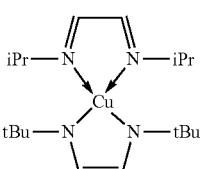

Compound No. 12

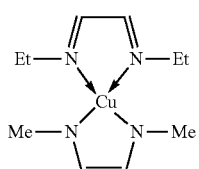

Compound No. 13

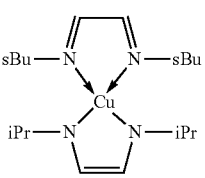

Compound No. 14

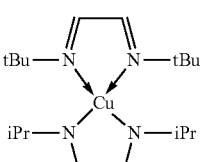

Compound No. 15

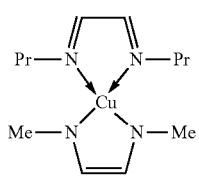

Compound No. 16

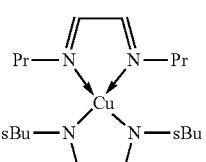

Compound No. 17

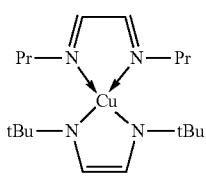

Compound No. 18

Preferred specific examples of the compound represented by the general formula (I) also include the compounds represented by chemical formulas No. 19 to No. 27 below, in which M is iron. In the chemical formulas No. 19 to No. 27, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 5]

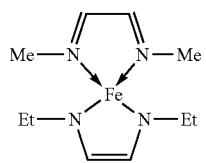

Compound No. 19

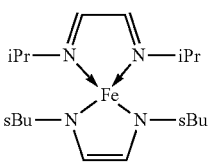

Compound No. 20

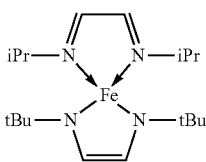

Compound No. 21

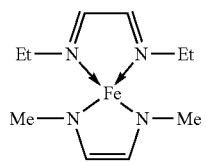

Compound No. 22

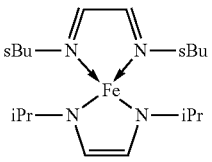

Compound No. 23

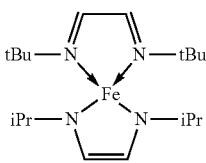

Compound No. 24

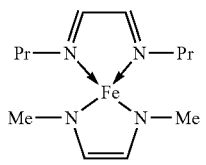

Compound No. 25

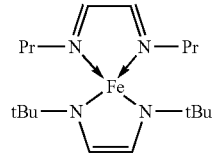

Compound No. 26

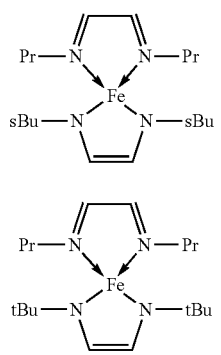

Compound No. 27

Preferred specific examples of the compound represented by the general formula (I) also include the compounds represented by chemical formulas No. 28 to No. 36 below, in which M is nickel. In the chemical formulas No. 28 to No. 36, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 6]

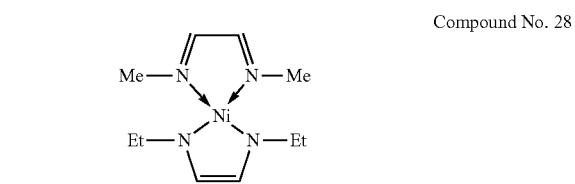

Compound No. 28

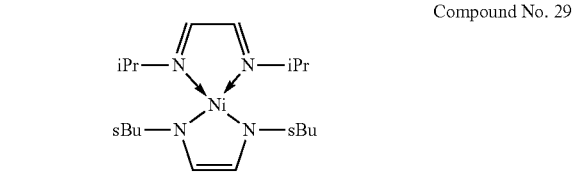

Compound No. 29

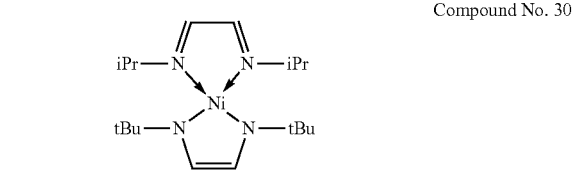

Compound No. 30

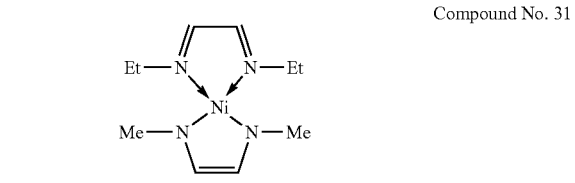

Compound No. 31

Compound No. 32

[Structure: Ni complex with sBu, sBu, iPr, iPr substituents]

Compound No. 33

[Structure: Ni complex with tBu, tBu, iPr, iPr substituents]

Compound No. 34

[Structure: Ni complex with Pr, Pr, Me, Me substituents]

Compound No. 35

[Structure: Ni complex with Pr, Pr, sBu, sBu substituents]

Compound No. 36

[Structure: Ni complex with Pr, Pr, tBu, tBu substituents]

Preferred specific examples of the compound represented by the general formula (I) also include the compounds represented by chemical formulas No. 37 to No. 45 below, in which M is manganese. In the chemical formulas No. 37 to No. 45, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 7]

Compound No. 37

[Structure: Mn complex with Me, Me, Et, Et substituents]

Compound No. 38

[Structure: Mn complex with iPr, iPr, sBu, sBu substituents]

Compound No. 39

[Structure: Mn complex with iPr, iPr, tBu, tBu substituents]

Compound No. 40

[Structure: Mn complex with Et, Et, Me, Me substituents]

Compound No. 41

[Structure: Mn complex with sBu, sBu, iPr, iPr substituents]

Compound No. 42

[Structure: Cu complex with tBu, tBu, iPr, iPr substituents]

Compound No. 43

[Structure: Mn complex with Pr, Pr, Me, Me substituents]

Compound No. 44

[Structure: Mn complex with Pr, Pr, sBu, sBu substituents]

Compound No. 45

[Structure: Mn complex with Pr, Pr, tBu, tBu substituents]

Preferred specific examples of the compound represented by the general formula (II) include the compounds represented by chemical formulas No. 46 to No. 51 below, in which M is cobalt. In the chemical formulas No. 46 to No. 51, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 8]

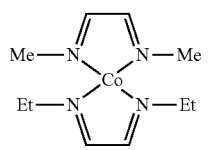
Compound No. 46

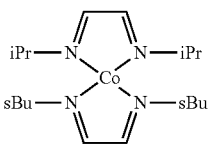
Compound No. 47

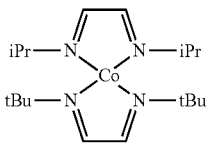
Compound No. 48

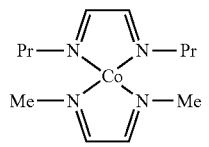
Compound No. 49

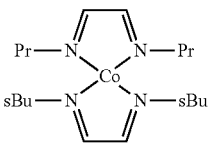
Compound No. 50

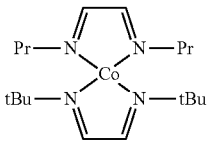
Compound No. 51

Preferred specific examples of the compound represented by the general formula (II) also include the compounds represented by chemical formulas No. 52 to No. 57 below, in which M is copper. In the chemical formulas No. 52 to No. 57, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 9]

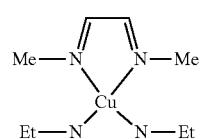
Compound No. 52

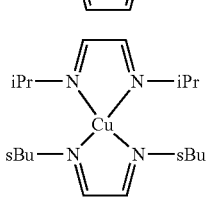
Compound No. 53

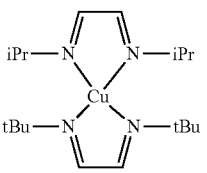
Compound No. 54

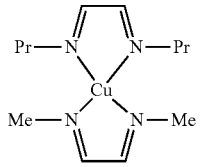
Compound No. 55

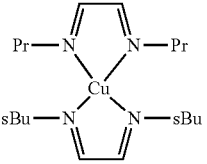
Compound No. 56

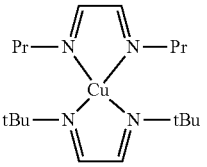
Compound No. 57

Preferred specific examples of the compound represented by the general formula (II) also include the compounds represented by chemical formulas No. 58 to No. 63 below, in which M is iron. In the chemical formulas No. 58 to No. 63, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 10]

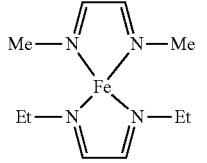
Compound No. 58

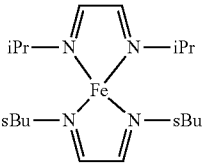
Compound No. 59

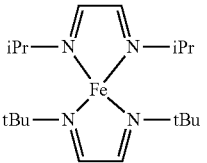
Compound No. 60

-continued

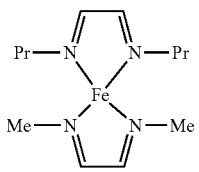

Compound No. 61

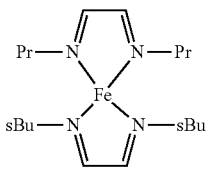

Compound No. 62

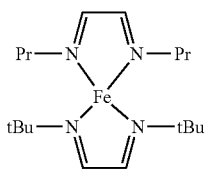

Compound No. 63

Preferred specific examples of the compound represented by the general formula (II) also include the compounds represented by chemical formulas No. 64 to No. 69 below, in which M is nickel. In the chemical formulas No. 64 to No. 69, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 11]

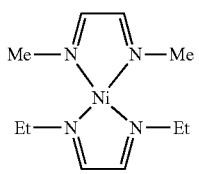

Compound No. 64

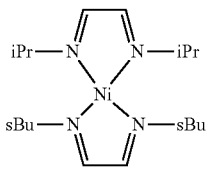

Compound No. 65

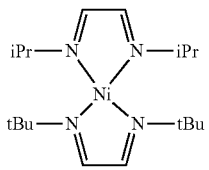

Compound No. 66

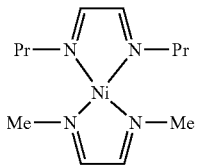

Compound No. 67

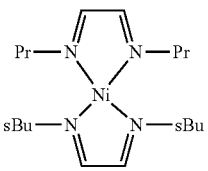

Compound No. 68

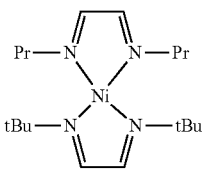

Compound No. 69

Preferred specific examples of the compound represented by the general formula (II) also include the compounds represented by chemical formulas No. 70 to No. 75 below, in which M is manganese. In the chemical formulas No. 70 to No. 75, "Me" represents a methyl group, "Et" represents an ethyl group, "Pr" represents a propyl group, "iPr" represents an isopropyl group, "sbu" represents a sec-butyl group and "tBu" represents a tert-butyl group.

[Chemical Formula 12]

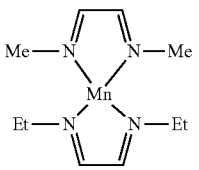

Compound No. 70

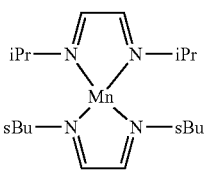

Compound No. 71

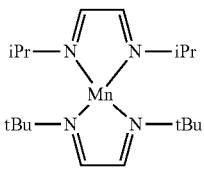

Compound No. 72

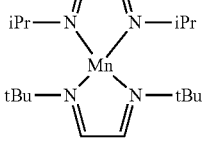

Compound No. 73

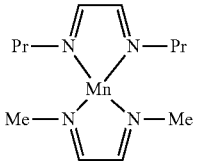

Compound No. 74

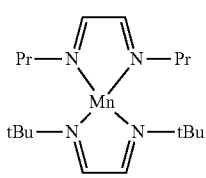
Compound No. 75

The compound of the invention is not particularly restricted by its manufacturing method, and may be manufactured by applying well-known reactions.

For example, of the compounds represented by the general formula (I) of the present invention, the cobalt compounds may be manufactured by a method in which a halide, nitrate salt or other inorganic salt of cobalt or a hydrate thereof is reacted with an applicable diazadiene compound; or by a method in which a halide, nitrate salt or other inorganic salt of cobalt or a hydrate thereof is reacted with an applicable diazadiene compound.

Moreover, of the compounds represented by the general formula (II) of the present invention, the cobalt diazadienyl compounds may be manufactured by a method in which a halide, nitrate salt or other inorganic salt of cobalt or a hydrate thereof is reacted with an applicable diazadiene compound in the presence of a base such as sodium, lithium, sodium hydride, sodium amide, sodium hydroxide, sodium methylate, ammonia or an amine; or by a method in which a halide, nitrate salt or other inorganic salt of cobalt or a hydrate thereof is reacted with a sodium complex, lithium complex, potassium complex or the like of an applicable diazadiene compound; or by disproportionating the compound represented by the general formula (I) of the present invention.

The thin film-forming material of the present invention has the compound of the invention as a thin film precursor, and the form of the thin film-forming material may be changed in various ways depending on the manufacturing process in which the thin film-forming material will be used. For example, when manufacturing a thin film containing only one kind of metal or silicon, the thin film-forming material of the present invention may not contain any metal compounds or semimetal compounds other than the aforementioned compound. When manufacturing a thin film containing two or more kinds of metals and/or semimetals, on the other hand, the thin film-forming material of the invention contains a compound (hereunder sometimes called the "other precursor") containing a desired metal and/or semimetal in addition to the aforementioned compound. Moreover, as discussed below, the thin film-forming material of the invention may also contain an organic solvent and/or a nucleophilic reagent. As explained above, because the compounds of the invention that can be used as precursors in the thin film-forming material of the invention have properties that are suited to CVD and ALD methods, the material is particularly useful as a material for chemical vapor deposition (hereunder sometimes called a "CVD material").

For example, when the thin film-forming material of the present invention is a material for chemical vapor deposition, the form of the thin film-forming material may be selected appropriately according to the transport supply methods and other techniques of the CVD method used.

Examples of CVD transport supply methods include gas transport methods in which a material for CVD method is heated and/or depressurized in a container in which the material is stored (sometimes called a "material container" below) to vaporize the material, and this vapor is then introduced together with a carrier gas such as argon, nitrogen or helium into a film-forming chamber (hereunder sometimes called a "deposition reaction unit") containing a substrate, and liquid transport methods in which a material for the CVD method is transported to a vaporizing chamber in a liquid or solution state, and heated and/or depressurized in the vaporizing chamber to vaporize the material that is then introduced into a film-forming chamber. In the case of a gas transport method, a compound represented by the general formula (I) or general formula (II) may itself be used as the material for the CVD method. In the case of a liquid transport method, a compound represented by the general formula (I) or general formula (II) above by itself or a solution of the compound dissolved in an organic solvent may be used as the material for the CVD method. These materials for the CVD method may also contain other precursors or nucleophilic reagents or the like.

Multicomponent CVD methods include methods of vaporizing and supplying each component of the material for CVD individually (hereunder sometimes called "single-source methods"), and methods of mixing the multicomponent material ahead of time in the desired composition to obtain a mixed material that is then vaporized and supplied (hereunder sometimes called "cocktail source methods"). In the case of a cocktail source method, a mixture of the compound of the present invention with another precursor or a mixed solution of this mixture dissolved in an organic solvent may be used as the material for the CVD. This mixture or mixed solution may also contain a nucleophilic reagent or the like.

The organic solvent is not particularly limited, and a commonly known organic solvent may be used. Examples of organic solvents include acetic acid esters such as ethyl acetate, butyl acetate and methoxyethyl acetate; ethers such as tetrahydrofuran, tetrahydropyran, ethylene glycol dimethyl ether, diethylene glycol dimethyl ether, triethylene glycol dimethyl ether, dibutyl ether and dioxane; ketones such as methyl butyl ketone, methyl isobutyl ketone, ethyl butyl ketone, dipropyl ketone, diisobutyl ketone, methyl amyl ketone, cyclohexanone and methyl cyclohexanone; hydrocarbons such as hexane, cyclohexane, methyl cyclohexane, dimethyl cyclohexane, ethyl cyclohexane, heptane, octane, toluene and xylene; hydrocarbons having cyano groups, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane and 1,4-dicyanobenzene; and pyridine, lutidine and the like, and one of these alone or a mixed solvent of two or more kinds may be used depending on the solubility of the solute and the relationship between usage temperature and boiling point or flash point.

When using these organic solvents, the total amount of the precursor in the material for the CVD method, which is a solution of the precursor dissolved in the organic solvent, is preferably 0.01 to 2.0 mol/liter, or especially 0.05 to 1.0 mol/liter. The total amount of the precursor is the amount of the compound of the present invention when the thin film-forming material of the invention does not include any metal compounds or semimetal compounds other than the compound of the invention, or the total amount of the compound of the present invention and the other precursor when the thin film-forming material of the present invention includes another metal-containing compound and/or another semimetal-containing compound in addition to the compound of the present invention.

In multicomponent CVD methods, the other precursor used together with the compound of the present invention is not particularly limited, and commonly known precursors used in materials for the CVD method may be used.

One or two or more silicon or metal compounds selected from the group consisting of the compounds having hydride, hydroxide, halide, azide, alkyl, alkenyl, cycloalkyl, aryl, alkynyl, amino, dialkylaminoalkyl, monoalkylamino, dialkylamino, diamine, di(silyl-alkyl)amino, di(alkyl-silyl)amino, disilylamino, alkoxy, alkoxyalkyl, hydrazide, phosphide, nitrile, dialkylaminoalkoxy, alkoxyalkyldialkylamino, siloxy, diketonate, cyclopentadienyl, silyl, pyrazolate, guanidinate, phosphoguanidinate, amidinate, phosphoamidinate, ketoiminate, diketiminate, carbonyl and phosphoamidinate ligands may be used as the other precursor.

The metal species of the other precursor may be magnesium, calcium, strontium, barium, radium, scandium, yttrium, titanium, zirconium, hafnium, vanadium, niobium, tantalum, chromium, molybdenum, tungsten, manganese, iron, osmium, cobalt, rhodium, iridium, nickel, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium or ytterbium.

The other precursor is one that is well known in the technical field, and whose manufacturing methods are also well known. As one example of a manufacturing method, using an alcohol compound as an organic ligand for example, an inorganic salt or hydrate thereof of one of the metals listed above may be reacted with an alkali metal alkoxide of the alcohol compound to manufacture the precursor. The inorganic salt or hydrate thereof of the metal may be a metal halide or nitrate salt or the like, and examples of alkali metal alkoxides include sodium alkoxide, lithium alkoxide and potassium alkoxide.

In the case of a single-source method, the other precursor is preferably a compound having similar behavior to the compound of the invention in terms of thermal and/or oxidative decomposition, while in the case of a cocktail source method, it is preferably one that not only has similar thermal and/or oxidative decomposition behavior, but also causes no change of properties due to chemical reactions and the like during mixing.

As the other precursor, examples of precursors containing titanium, zirconium or hafnium include the compounds represented by the following formulas (II-1) to (II-5):

[Chemical Formula 13]

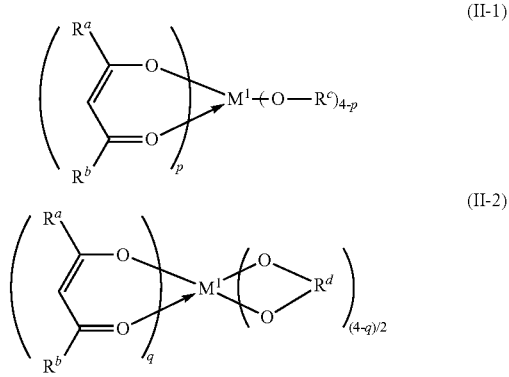

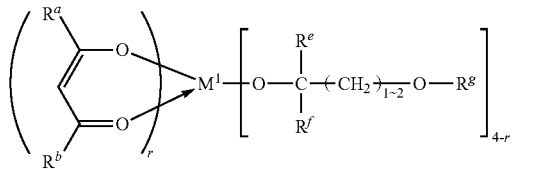

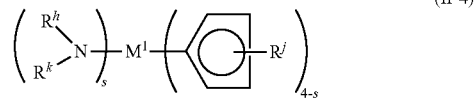

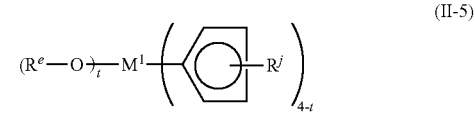

(In the formulas, $M^1$ represents titanium, zirconium or hafnium, each of $R^a$ and $R^b$ independently represents a $C_{1\sim20}$ alkyl group optionally substituted with a halogen atom and optionally having an oxygen atom in the molecular chain, $R^c$ represents a $C_{1\sim8}$ alkyl group, $R^d$ represents A $C_{2\sim18}$ optionally branched alkylene group, each of $R^e$ and $R^f$ independently represents a hydrogen atom or $C_{1\sim3}$ alkyl group, each of $R^g$, $R^h$, $R^k$ and $R^j$ independently represents a hydrogen atom or $C_{1\sim4}$ alkyl group, p is an integer from 0 to 4, q is 0 or 2, r is an integer from 0 to 3, s is an integer from 0 to 4 and t is an integer from 1 to 4.)

In the formulas (II-1) to (II-5) above, examples of the $C_{1\sim20}$ alkyl groups optionally substituted with a halogen atom and optionally having an oxygen atom in the molecular chain represented by $R^a$ and $R^b$ include methyl, ethyl, propyl, isopropyl, butyl, sec-butyl, tert-butyl, isobutyl, amyl, isoamyl, sec-amyl, tert-amyl, hexyl, cyclohexyl, 1-methylcyclohexyl, heptyl, 3-heptyl, isoheptyl, tert-heptyl, n-octyl, isooctyl, tert-octyl, 2-ethylhexyl, trifluoromethyl, perfluorohexyl, 2-methoxyethyl, 2-ethoxyethyl, 2-butoxyethyl, 2-(2-methoxyethoxy)ethyl, 1-methoxy-1,1-dimethylmethyl, 2-methoxy-1,1-dimethylethyl, 2-ethoxy-1,1-dimethylethyl, 2-isopropoxy-1,1-dimethylethyl, 2-butoxy-1,1-dimethylethyl, 2-(2-methoxyethoxy)-1,1-dimethylethyl and the like. Examples of the $C_{1\sim8}$ alkyl group represented by $R^c$ include methyl, ethyl, propyl, isopropyl, butyl, sec-butyl, tert-butyl, isobutyl, amyl, isoamyl, sec-amyl, tert-amyl, hexyl, 1-ethylpentyl, cyclohexyl, 1-methylcyclohexyl, heptyl, isoheptyl, tert-heptyl, n-octyl, isooctyl, tert-octyl, 2-ethylhexyl and the like. The $C_{2\sim18}$ optionally branched alkylene group represented by $R^d$ is a group provided by a glycol, and examples of this glycol include 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, 1-methyl-2,4-pentanediol and the like. Examples of the $C_{1\sim3}$ alkyl groups represented by $R^e$ and $R^f$ include methyl, ethyl, propyl, 2-propyl and the like, while examples of the $C_{1\sim4}$ alkyl groups represented by $R^g$, $R^h$, $R^j$ and $R^k$ include methyl, ethyl, propyl, isopropyl, butyl, sec-butyl, tert-butyl, isobutyl and the like.

Specific examples of other precursors containing titanium include tetrakis alkoxy titanium compounds such as tetrakis (ethoxy)titanium, tetrakis(2-propoxy)titanium, tetrakis(butoxy)titanium, tetrakis(sec-butoxy)titanium, tetrakis(isobutoxy)titanium, tetrakis(tert-butoxy)titanium, tetrakis(tert-amyl)titanium and tetrakis(1-methoxy-2-methyl-2-propoxy) titanium; tetrakis β-diketonate titanium compounds such as tetrakis(pentane-2,4-dionato)titanium, (2,6-dimethylheptane-3,5-dionato)titanium and tetrakis(2,2,6,6-tetramethylheptane-3,5-dionato)titanium; bis(alkoxy)bis(β-diketonato) titanium compounds such as bis(methoxy)bis(pentane-2,4-dionato)titanium, bis(ethoxy)bis(pentane-2,4-dionato) titanium, bis(tert-butoxy)bis(pentane-2,4-dionato)titanium, bis(methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato) titanium, bis(tert-amyloxy)bis(2,6-dimethylheptane-3,5-dionato)titanium, bis(methoxy)bis(2,2,6,6-tetramethylheptane-3,5-dionato)titanium, bis(ethoxy)bis(2,2,6,6-tetramethylheptane-3,5-dionato)titanium, bis(2-propoxy)bis(2,6,6,6-tetramethylheptane-3,5-dionato) titanium, bis(tert-butoxy)bis(2,2,6,6-tetramethylheptane-3,5-dionato)titanium and bis(tert-amyloxy)bis(2,2,6,6-tetramethylheptane-3,5-dionato)titanium; glycoxybis(β-diketonato)titanium compounds such as (2-methylpentanedioxy)bis(2,2,6,6-tetramethylheptane-3,5-dionato)titanium and (2-methylpentanedioxy)bis(2,6-dimethylheptane-3,5-dionato)titanium; (cyclopentadienyl)tris (dialkylamino)titanium compounds such as (methylcyclopentadienyl)tris(dimethylamino)titanium, (ethylcyclopentadienyl)tris(dimethylamino)titanium, (cyclopentadienyl)tris(dimethylamino)titanium, (methylcyclopentadienyl)tris(ethylmethylamino)titanium, (ethylcyclopentadienyl)tris(ethylmethylamino)titanium, (cyclopentadienyl)tris(ethylmethylamino)titanium, (methylcyclopentadienyl)tris(diethylamino)titanium, (ethylcyclopentadienyl)tris(diethylamino)titanium and (cyclopentadienyl)tris(diethylamino)titanium; and (cyclopentadienyl)tris (alkoxy)titanium compounds such as (cyclopentadienyl)tris (methoxy)titanium, (methylcyclopentadienyl)tris(methoxy) titanium, (ethylcyclopentadienyl)tris(methoxy)titanium, (propylcyclopentadienyl)tris(methoxy)titanium, (isopropylcyclopentadienyl)tris(methoxy)titanium, (butylcyclopentadienyl)tris(methoxy)titanium, (isobutylcyclopentadienyl) tris(methoxy)titanium, tert-butylcyclopentadienyl)tris (methoxy)titanium and (pentamethylcyclopentadienyl)tris (methoxy)titanium, while examples of precursors containing zirconium or precursors containing hafnium include compounds obtained by substituting zirconium or hafnium for the titanium in the compounds given above as examples of precursors containing titanium.

Examples of other precursors containing rare earth elements include the compounds represented by the following formulas (III-1) to (III-3):

[Chemical Formula 14]

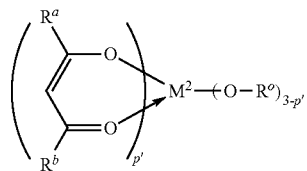

(III-1)

(III-2)

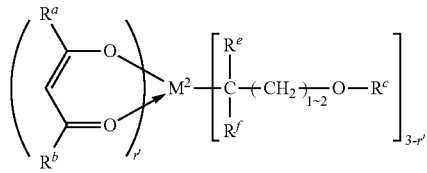

(III-3)

(In the formulas, $M^2$ represents a rare earth atom, each of $R^a$ and $R^b$ independently represent a $C_{1-20}$ alkyl group optionally substituted with a halogen atom and optionally having an oxygen atom in the molecular chain, $R^c$ represents a $C_{1-8}$ alkyl group, each of $R^e$ and $R^f$ independently represent a hydrogen atom or $C_{1-3}$ alkyl group, each of $R^g$ and $R^j$ independently represent a hydrogen atom or $C_{1-4}$ alkyl group, p' is an integer from 0 to 3, and r' is an integer from 0 to 2.)

Examples of the rare earth element represented by $M^2$ in the other precursor containing a rare earth element include scandium, yttrium, lanthanum, cerium, praseodymium, neodymium, promethium, samarium, europium, gadolinium, terbium, dysprosium, holmium, erbium, thulium, ytterbium and lutetium, while examples of the groups represented by $R^a$, $R^b$, $R^c$, $R^e$, $R^f$, $R^g$ and $R^j$ include those given as examples in the other precursor containing titanium above.

The thin film-forming material of the present invention may also contain a nucleophilic reagent as necessary in order to confer stability on the compound of the present invention and the other precursor. Examples of this nucleophilic reagent include ethylene glycol ethers such as glyme, diglyme, triglyme and tetraglyme, crown ethers such as 18-crown-6, dicyclohexyl-18-crown-6, 24-crown-8, dicyclohexyl-24-crown-8 and dibenzo-24-crown-8, polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine and triethoxytriethylenamine, cyclic polyamines such as cyclam and cyclen, heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole and oxathiolane, β-keto esters such as methyl acetoacetate, ethyl acetoacetate and 2-methoxyethyl acetoacetate, or β-diketones such as acetylacetone, 2,4-hexanedione, 2,4-heptanedione, 3,5-heptanedione and dipivaloylmethane, and these nucleophilic reagents are used in the amount of preferably 0.1 to 10 moles, or more preferably 1 to 4 moles per 1 mole of the precursor as a whole.

Apart from the components constituting the material, the thin film-forming material of the present invention preferably contains as little metal elemental impurities, halogen impurities such as chlorine, and organic impurities as possible. The amount of the metal elemental impurities is preferably not more than 100 ppb, or more preferably not more than 10 ppb per element, and preferably not more than 1 ppm or more preferably not more than 100 ppb in total. It is particularly necessary to minimize the content of alkali metal elements and alkali earth metal elements, which can affect the electrical characteristics of the resulting thin film when it is used as an LSI gate insulating film, gate film or barrier layer. The content of halogen impurities is preferably not more than 100 ppm, or more preferably not more than 10 ppm, or still more preferably not more than 1 ppm. The total content of organic impurities is preferably not more than 500 ppm, or more preferably not more than 50 ppm, or still more preferably not more than 10 ppm.

Moreover, because moisture can cause particle generation in the material for chemical vapor deposition or particle generation during thin film formation, the moisture in the metal compound, the organic solvent and the nucleophilic reagent is preferably removed ahead of time in order to reduce the moisture content of each for purposes of use. The respective moisture content of the metal compound, organic solvent and nucleophilic reagent is preferably not more than 10 ppm, or more preferably not more than 1 ppm.

Furthermore, the thin film-forming material of the present invention preferably contains as few particles as possible in order to reduce or prevent particle contamination of the formed thin film. Specifically, the number of particles larger than 0.3 μm is preferably not more than 100, and more preferably the number of particles larger than 0.2 μm is not more than 1,000, and still more preferably the number of particles larger than 0.2 μm is not more than 100 per 1 ml of liquid phase in particle measurement of the liquid phase with a light scattering-type in-liquid particle detector.

The thin film manufacturing method of the present invention in which a thin film is manufactured using the thin film-forming material of the present invention is a CVD method of deposition whereby the thin film-forming material of the present invention is vaporized into a vapor that is introduced together with a reactive gas as necessary into a film-forming chamber containing a substrate, and the precursor is then decomposed and/or chemically reacted on the substrate to grow and deposit a thin film containing a metal on the surface of the substrate. The material transport supply method, deposition method, manufacturing conditions, manufacturing equipment and the like are not particularly limited, and ordinary well-known conditions and methods may be applied.

Examples of the reactive gas that is used as necessary above include oxidizing gases such as oxygen, ozone, nitrogen dioxide, nitrogen monoxide, water vapor, hydrogen peroxide, formic acid, acetic acid, acetic anhydride and the like, and reducing gases such as hydrogen, as well as organic amine compounds such as monoalkylamine, dialkylamine, trialkylamine and alkylenediamine and hydrazine and ammonia when manufacturing a nitride, and one of these or two or more may be used.

Examples of the transport supply method include gas transport methods, liquid transport methods, single-source methods and cocktail source methods as discussed above.

Examples of the deposition method include thermal CVD, in which a material gas or a material gas and a reactive gas are reacted by heat alone to deposit a thin film, plasma CVD method using heat and plasma, optical CVD method using heat and light, optical-plasma CVD method using heat, light and plasma, and ALD method, in which the CVD deposition reaction is divided into elemental processes and deposition is carried out in stages at an atomic level.

The material of the substrate may be, for example, silicon; a ceramic such as silicon nitride, titanium nitride, tantalum nitride, titanium oxide, titanium nitride, ruthenium oxide, zirconium oxide, hafnium oxide or lanthanum oxide; glass; or a metal such as ruthenium metal. The shape of the substrate may be plate-shaped, spherical, fibrous or scale-shaped, and the substrate surface may be flat or have a trench structure or other three-dimensional structure.

The manufacturing conditions include reaction temperature (substrate temperature), reaction pressure, deposition rate and the like. The reaction temperature is preferably at least 100° C., which is the temperature at which the compound of the invention reacts sufficiently, or more preferably 150° C. to 400° C. Since the compound of the present invention can be thermally decomposed at temperatures below 250° C., a temperature of 150° C. to 250° C. is especially desirable. The reaction pressure is preferably between atmospheric pressure and 10 Pa in the case of a thermal CVD method or optical CVD method, or 2,000 Pa to 10 Pa when using plasma.

The deposition rate can be controlled by means of the material supply conditions (vaporization temperature, vaporization pressure), the reaction temperature and the reaction pressure. If the deposition rate is high the properties of the resulting thin film may be poor, while if it is low there may be problems of productivity, so a deposition rate of 0.01 to 100 nm/min is preferred, and 1 to 50 nm/min is more preferred. In the case of an ALD method, the number of cycles is controlled so as to obtain the desired film thickness.

Other manufacturing conditions include the temperature and pressure when vaporizing the thin film-forming material into a vapor. The step of vaporizing the thin film-forming material into a vapor may be performed either in a material container or in a vaporization chamber. In either case, the thin film-forming material of the present invention is preferably vaporized at 0° C. to 150° C. When vaporizing the thin film-forming material into a vapor in a material container or vaporization chamber, the pressure inside the material container or the pressure inside the vaporization chamber is preferably 1 to 10,000 Pa in either case.

Using an ALD method, the thin film manufacturing method of the present invention may comprise a material introduction step in which the thin film-forming material is vaporized into a vapor and introduced into a film-forming chamber by the transport supply method described above, as well as a precursor thin film-forming step in which a precursor thin film is formed on the surface of the substrate by the compound in the vapor, an exhaust step in which unreacted compound gas is exhausted, and a metal-containing thin film-forming step in which the precursor thin film is chemically reacted with a reactive gas to thereby form a thin film containing the metal on the surface of the substrate.

Each of these steps is explained in detail below using the example of a metal oxide thin film. When forming a metal oxide thin film by an ALD method, the material introduction step explained above is performed first. The preferred temperature and pressure when vaporizing the thin film-forming material are similar to those explained above. Next, a precursor thin film is formed on the surface of the substrate by the compound introduced into the deposition reaction unit (precursor thin film-forming step). During this process, heat may be applied either by heating the substrate or by heating the deposition reaction unit. The precursor thin film formed in this step is a metal oxide thin film or a thin film produced by decomposition and/or reaction of part of the compound, and has a composition different from that of the target metal oxide thin film. The substrate temperature during this step is preferably room temperature to 500° C., or more preferably 150° C. to 350° C. The pressure of the system (film-forming chamber interior) during this step is preferably 1 to 10,000 Pa, or more preferably 10 to 1,000 Pa.

Next, the unreacted compound gas and bi-product gas are exhausted from the deposition reaction unit (exhaust step) Ideally the unreacted compound gas and bi-product gas are completely exhausted from the deposition reaction unit, but they do not have to be absolutely completely exhausted. Exhaust methods include methods of purging the system with a non-reactive gas such as nitrogen, helium or argon, methods of exhausting by depressurizing the system, and combinations of these. In the case of depressurization, the degree of depressurization is preferably 0.01 to 300 Pa, or more preferably 0.01 to 100 Pa.

Next, an oxidizing gas is introduced into the deposition reaction unit, and a metal oxide thin film is formed from the precursor thin film obtained in the previous precursor thin film-forming step by the action of the oxidizing gas or the action of the oxidizing gas and heat (metal oxide-containing thin film-forming step). When heat is applied in this step, the temperature is preferably room temperature to 500° C., or more preferably 150° C. to 350° C. The pressure of the system (film-forming chamber interior) during this step is preferably 1 to 10,000 Pa, or more preferably 10 to 1,000 Pa. The compound of the invention has good reactivity with reducing gasses, and can yield a metal thin film.

In the thin film manufacturing method of the present invention, using an ALD method as described above, thin film deposition by a series of procedures consisting of the material introduction step, precursor thin film-forming step, exhaust step and metal oxide-containing thin film-forming step as described above is called one cycle, and this cycle is repeated multiple times until a thin film of the necessary film thickness is obtained. In this case, after one cycle is performed, unreacted compound gas, reactive gas (oxidizing gas when forming a metal oxide thin film) and bi-product gas are preferably exhausted from the deposition reaction unit as in the exhaust step above before performing the next cycle.

Energy in the form of plasma, light, voltage or the like may also be applied when forming a metal oxide thin film by an ALD method, and a catalyst may also be used. The period for applying the energy and the period for using the catalyst are not particularly limited, and may be for example during compound gas introduction in the material introduction step, during heating in the precursor thin film-forming step or metal oxide-containing thin film-forming step, when exhausting the system in the exhaust step, during oxidizing gas introduction in the metal oxide-containing thin film-forming step, or between any of these steps.

To obtain better electrical characteristics, annealing may also be performed in the thin film manufacturing method of the present invention after thin film deposition in an inactive atmosphere, oxidizing atmosphere or reducing atmosphere, and a reflow step may also be included when level embedding is required. The temperature in this case is 200° C. to 1,000° C., or preferably 250° C. to 500° C.

Figure 2:
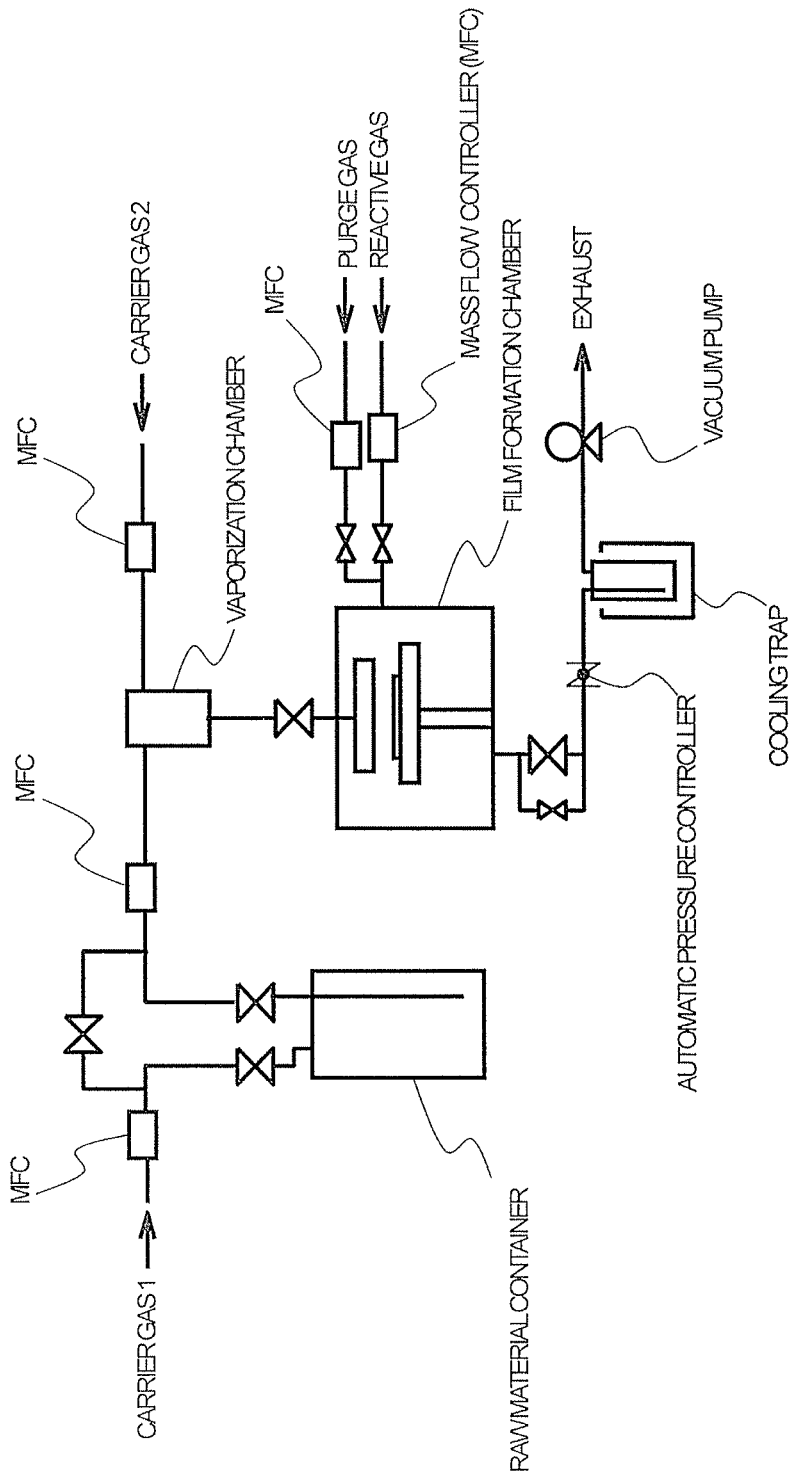
FIG. 2 is an outline drawing showing another embodiment of a chemical vapor deposition apparatus that can be used in the thin film manufacturing method of the present invention.
Figure 3:
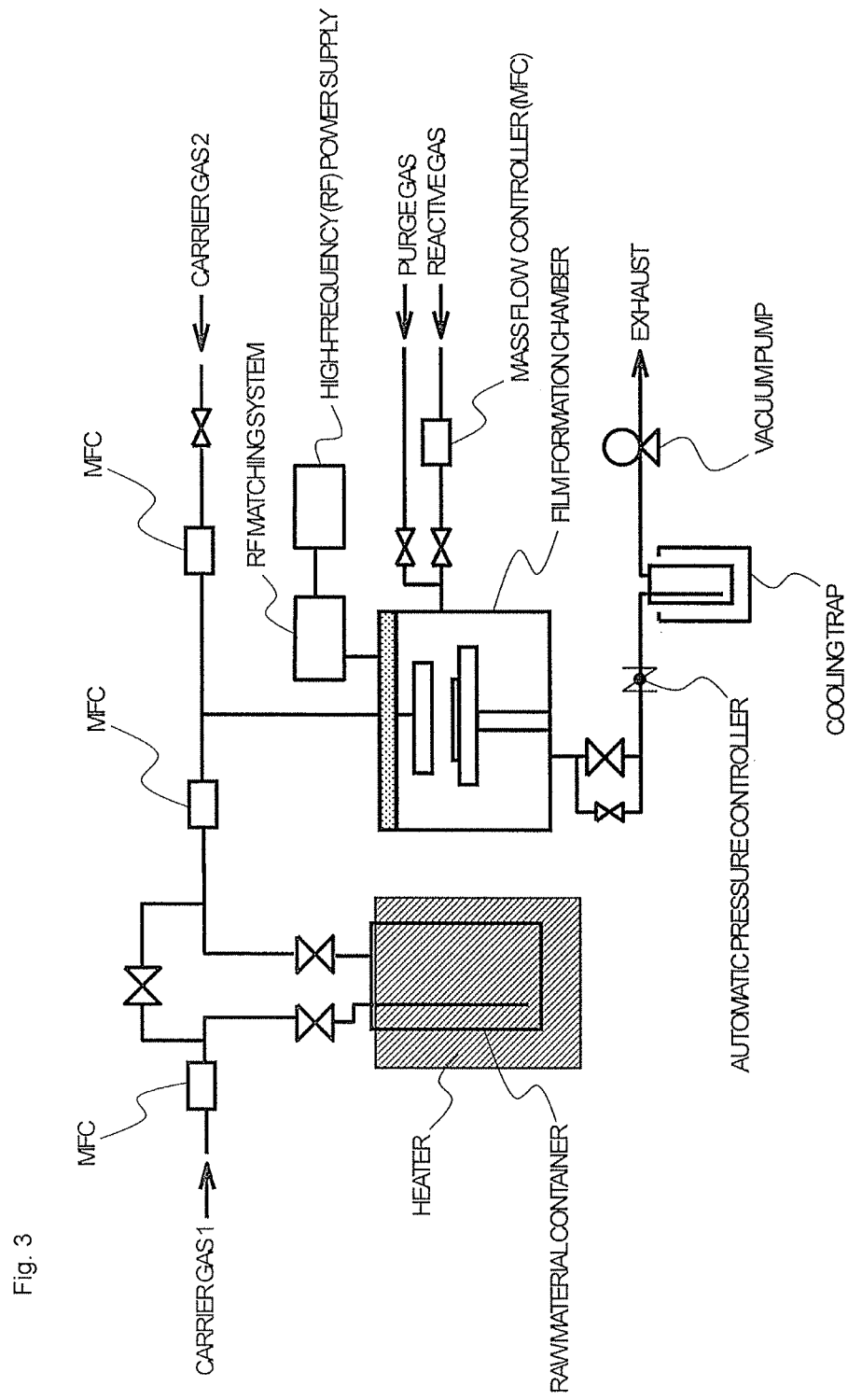
FIG. 3 is an outline drawing showing yet another embodiment of a chemical vapor deposition apparatus that can be used in the thin film manufacturing method of the present invention.
Figure 4:
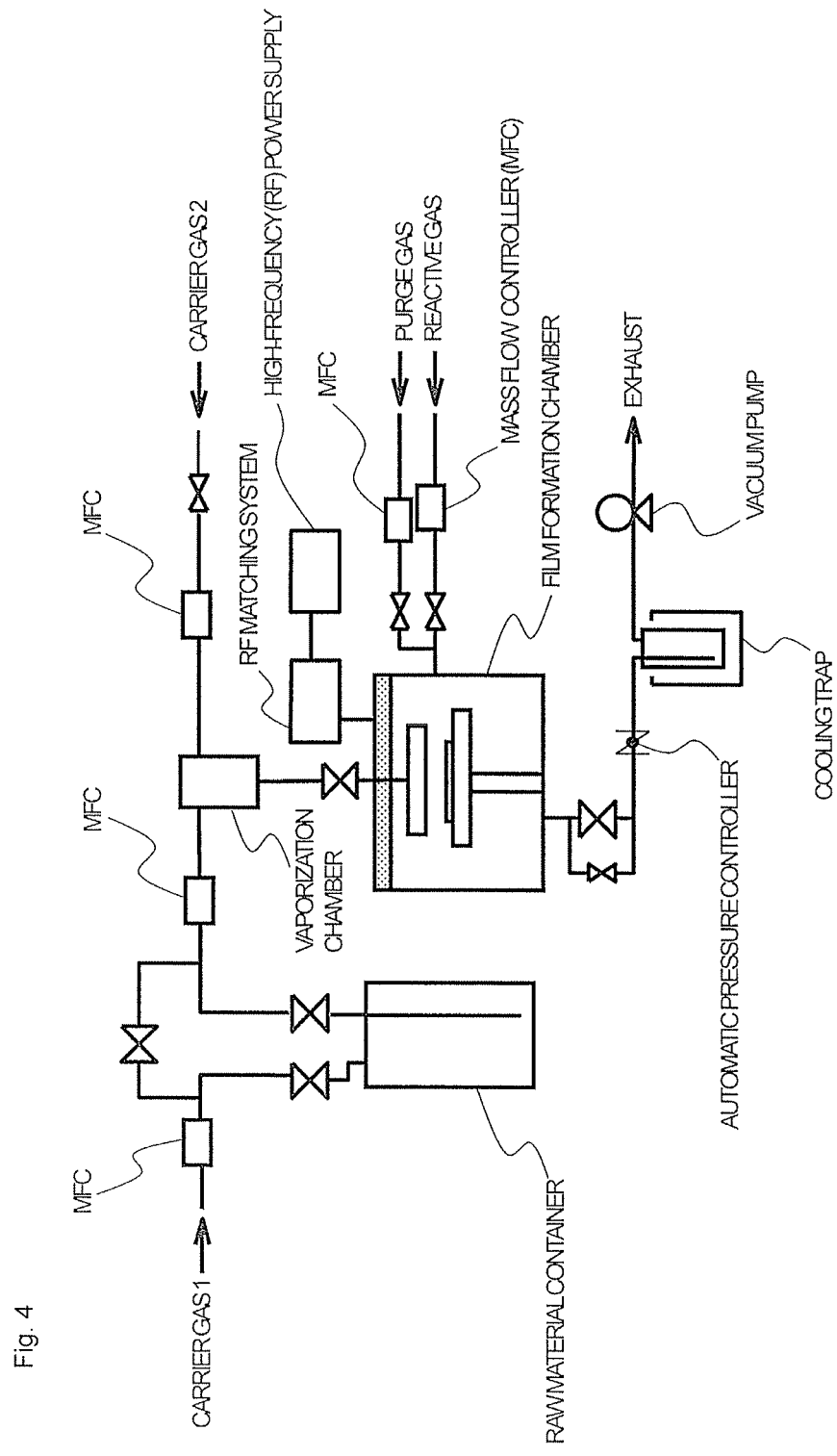
FIG. 4 is an outline drawing showing yet another embodiment of a chemical vapor deposition apparatus that can be used in the thin film manufacturing method of the present invention.

A known machine for chemical vapor deposition may be used as the equipment for manufacturing a thin film using the thin film-forming material of the present invention. Specific examples include a machine such as that shown in FIG. 1, which can form the precursor by bubbling supply, and machine such as that shown in FIG. 2 having a vaporization chamber. Other examples include machines such as those shown in FIG. 3 and FIG. 4, which perform plasma treatment with a reactive gas. Besides single wafer type machines such as those shown in FIGS. 1 to 4, it is also possible to use a machine that uses a batch furnace to simultaneously treat multiple wafers.

A thin film manufactured using the thin film-forming material of the present invention can be obtained as the desired type of thin film, such as a metal, oxide ceramic, nitride ceramic and glass, by appropriately selecting the other precursor, reactive gas and manufacturing conditions. Thin films are known to exhibit various electrical and optical characteristics and the like, and are used in various applications. For example, copper thin films and copper-containing thin films are applied as LSI wiring materials due to their properties of high electrical conductivity, electromigration resistance and high melting point. Nickel thin films and nickel-containing thin films are used mainly for electronic components such as low resistance films and barrier films, for recording media components such as magnetic films, and for thin film solar cell components such as electrodes. Cobalt thin films and cobalt-containing thin films are used for electrode films, low resistance film, adhesive films, magnetic tapes, ultrahard tool materials and the like.

EXAMPLES

The present invention is explained in more detail below using examples and evaluation examples. However, the present invention is in no way limited by these examples and the like.

Example 1: Manufacture of Compound No. 2

5.02 g (0.039 mol) of cobalt (II) chloride and 19.5 g of tetrahydrofuran were loaded into a 200 ml 4-necked flask, and stirred at room temperature. A solution prepared from 5.47 g (0.039 mol) of N,N'-diisopropyl-1,4-diaza-1,3-butadiene and 40.5 g of tetrahydrofuran was added dropwise under ice cooling. Next, a solution prepared from 7.50 g (0.044 mol) of N,N'-di-sec-butyl-1,4-diaza-1,3-butadiene, 39.1 g of tetrahydrofuran and 0.59 g (0.085 mol) of Li was added dropwise, and after dropping the mixture was returned to room temperature, stirred for 17 hours, and filtered. The solvent was removed from the resulting filtrate, and the residue was distilled at a bath temperature of 140° C., a pressure of 96 Pa and a column top temperature of 120° C. to obtain a dark brown liquid. The yield was 8.20 g and the percentage yield was 58%.

(Analysis Values)
(1) Normal Pressure TG-DTA
50% mass reduction temperature: 226° C. (Ar flow: 100 ml/min, temperature rise 10° C./min, sample volume: 9.766 mg)
(2) Reduced Pressure TG-DTA
50% mass reduction temperature: 145° C. (10 Torr, Ar flow: 50 ml/min, temperature rise 10° C./min, sample volume: 9.821 mg)
(3) Elemental Analysis (Metal Analysis: ICP-AES)
Cobalt content: 16.5 mass % (theoretical value 16.04 mass %)
CHN analysis: C, 59.6%; (theoretical value 58.9%), H, 10.0%; (theoretical value 9.9%), N, 15.1%; (theoretical value 15.3%).

Example 2: Manufacture of Compound No. 3

10.0 g (0.077 mol) of cobalt (II) chloride and 54.2 g of tetrahydrofuran were loaded into a 300 ml 4-necked flask, and stirred at room temperature. A solution prepared from 10.9 g (0.078 mol) of N,N'-diisopropyl-1,4-diaza-1,3-butadiene and 67.7 g of tetrahydrofuran was added dropwise under ice cooling. Next, a solution prepared from 14.3 g (0.085 mol) of N,N'-di-tert-butyl-1,4-diaza-1,3-butadiene, 82.9 g of tetrahydrofuran and 1.19 g (0.17 mol) of Li was added dropwise, and after dropping the mixture was returned to room temperature and stirred for 15 hours. The solvent was distilled off at a bath temperature of 100° C. under slightly reduced pressure, solvent substitution was performed with n-heptane, and the mixture was filtered. The solvent was removed from the resulting filtrate, and the residue was distilled at a bath temperature of 140° C., a pressure of 54 Pa and a column top temperature of 114° C. to obtain a deep brown solid. The yield was 23.2 g, and the percentage yield was 82%.
(Analysis Values)
(1) Normal Pressure TG-DTA
  50% mass reduction temperature: 231° C. (Ar flow: 100 ml/min, temperature rise 10° C./min, sample volume: 10.21 mg)
(2) Reduced Pressure TG-DTA
  50% mass reduction temperature: 146° C. (10 Torr, Ar flow: 50 ml/min, temperature rise 10° C./min, sample volume: 9.324 mg)
(3) Elemental Analysis (Metal Analysis: ICP-AES)
  Cobalt content: 16.0 mass % (theoretical value 16.04 mass %)
  CHN analysis: C, 59.0%; (theoretical value 58.9%), H, 10.0%; (theoretical value 9.9%), N, 15.1%; (theoretical value 15.3%).

Example 3: Manufacture of Compound No. 5

5.09 g (0.039 mol) of cobalt (II) chloride and 44.6 g of tetrahydrofuran were loaded into a 200 ml 4-necked flask, and stirred at room temperature. 6.65 g (0.039 mol) of N,N'-di-sec-butyl-1,4-diaza-1,3-butadiene was added dropwise to this under ice cooling. Next, a solution prepared from 5.97 g (0.042 mol) of N,N'-diisopropyl-1,4-diaza-1,3-butadiene, 38.0 g of tetrahydrofuran and 0.59 g (0.085 mol) of Li was added dropwise, and after dropping the mixture was returned to room temperature, stirred for 21 hours, and filtered. The solvent was removed from the resulting filtrate, and the residue was distilled at a bath temperature of 145° C., a pressure of 90 Pa and a column top temperature of 129° C. to obtain a dark brown liquid. The yield was 7.28 g, and the percentage yield was 51%.
(Analysis Values)
(1) Normal Pressure TG-DTA
  50% mass reduction temperature: 230° C. (Ar flow: 100 ml/min, temperature rise 10° C./min, sample volume: 9.737 mg)
(2) Reduced Pressure TG-DTA
  50% mass reduction temperature: 149° C. (10 Torr, Ar flow: 50 ml/min, temperature rise 10° C./min, sample volume: 9.802 mg)
(3) Elemental Analysis (Metal Analysis: ICP-AES)
  Cobalt content: 16.2 mass % (theoretical value 16.04 mass %)
  CHN analysis: C, 58.1%; (theoretical value 58.9%), H, 9.3%; (theoretical value 9.9%), N, 15.1%; (theoretical value 15.7%).

Example 4: Manufacture of Compound No. 6

15.0 g (0.12 mol) of cobalt (II) chloride and 45.6 g of tetrahydrofuran were loaded into a 500 ml 4-necked flask, and stirred at room temperature. A solution prepared from 19.7 g (0.12 mol) of N,N'-di-tert-butyl-1,4-diaza-1,3-butadiene and 81.9 g of tetrahydrofuran was then added dropwise under ice cooling. Next, a solution prepared from 17.8 g (0.12 mol) of N,N'-diisopropyl-1,4-diaza-1,3-butadiene, 121 g of tetrahydrofuran and 1.76 g (0.25 mol) of Li was added dropwise, and after dropping the mixture was returned to room temperature and stirred for 18 hours. The solvent was distilled off at a bath temperature of 95° C. under slightly reduced pressure, solvent substitution was performed with n-heptane, and the mixture was filtered. The solvent was removed from the resulting filtrate, and the residue was distilled at a bath temperature of 140° C., a pressure of 110 Pa and a column top temperature of 133° C. to obtain a deep brown solid. The yield was 25.4 g, and the percentage yield was 60%.
(Analysis Values)
(1) Normal Pressure TG-DTA
  50% mass reduction temperature: 227° C. (Ar flow: 100 ml/min, temperature rise 10° C./min, sample volume: 10.00 mg)
(2) Reduced Pressure TG-DTA
  50% mass reduction temperature: 144° C. (10 Torr, Ar flow: 50 ml/min, temperature rise 10° C./min, sample volume: 10.07 mg)
(3) Elemental Analysis (Metal Analysis: ICP-AES)
  Cobalt content: 16.1 mass % (theoretical value 16.04 mass %)
  CHN analysis: C, 58.7%; (theoretical value 58.9%), H, 9.2%; (theoretical value 9.9%), N, 15.9%; (theoretical value 15.3%).

Example 5: Manufacture of Compound No. 9

5.05 g (0.039 mol) of cobalt (II) chloride and 43.3 g of tetrahydrofuran were loaded into a 200 ml 4-necked flask, and stirred at room temperature. 5.60 g (0.040 mol) of N,N'-di-n-propyl-1,4-diaza-1,3-butadiene were added dropwise to this under ice cooling. Next, a solution prepared from 7.36 g (0.044 mol) of N,N'-di-tort-butyl-1,4-diaza-1,3-butadiene, 40.8 g of tetrahydrofuran and 0.59 g (0.085 mol) of Li was added dropwise, and after dropping the mixture was returned to room temperature and stirred for 17 hours. The solvent was distilled off at a bath temperature of 90° C. under slightly reduced pressure, solvent substitution was performed with n-heptane, and the mixture was filtered. The solvent was removed from the resulting filtrate, and the residue was distilled at a bath temperature of 145° C., a pressure of 56 Pa and a column top temperature of 110° C. to obtain a deep green liquid. The yield was 6.97 g, and the percentage yield was 49%.
(Analysis Values)
(1) Normal Pressure TG-DTA
  50% mass reduction temperature: 227° C. (Ar flow: 100 ml/min, temperature rise 10° C./min, sample volume: 9.688 mg)
(2) Reduced Pressure TG-DTA
  50% mass reduction temperature: 146° C. (10 Torr, Ar flow: 50 ml/min, temperature rise 10° C./min, sample volume: 10.31 mg)
(3) Elemental Analysis (Metal Analysis: ICP-AES)
  Cobalt content: 16.2 mass % (theoretical value 16.04 mass %)
  CHN analysis: C, 58.2%; (theoretical value 58.9%), H, 9.3%; (theoretical value 9.9%), N, 15.7%; (theoretical value 15.3%).

Example 6: Manufacture of Compound No. 30

4.0 g (0.031 mol) of nickel (II) chloride and 23.8 g of tetrahydrofuran were loaded into a 200 ml 4-necked flask, and stirred at room temperature. A solution prepared from 4.33 g (0.031 mol) of N,N'-diisopropyl-1,4-diaza-1,3-butadiene and 19.7 g of tetrahydrofuran was added dropwise to this under ice cooling. Next, a solution prepared from 5.19 g (0.031 mol) of N,N'-di-tert-butyl-1,4-diaza-1,3-butadiene, 37.4 g of tetrahydrofuran and 0.42 g (0.062 mol) of Li was added dropwise, and after dropping the mixture was returned to room temperature and stirred for 20 hours. The solvent was distilled off at a bath temperature of 70° C. under slightly reduced pressure, solvent substitution was performed with n-hexane, and the mixture was filtered. The solvent was removed from the resulting filtrate, and the residue was purified under conditions of 105° C., 30 Pa with a Kugelrohr to obtain a dark red solid. The yield was 1.81 g, and the percentage yield was 16%.

(Analysis Values)
(1) Normal Pressure TG-DTA
  50% mass reduction temperature: 210° C. (Ar flow: 100 ml/min, temperature rise 10° C./min, sample volume: 9.980 mg)
(2) Reduced Pressure TG-DTA
  50% mass reduction temperature: 142° C. (10 Torr, Ar flow: 50 ml/min, temperature rise 10° C./min, sample volume: 9.698 mg)
(3) $^1$H-NMR (Solvent: Heavy Benzene) (Chemical Shift: Multiplicity:H Number)
  (8.934-8.948:d:2) (8.733-8.738:d:2) (2.785-2.834:m:1) (2.603-2.667:m:1) (1.941:s:9) (1.908-1.925:d:6) (1.899:s:9) (1.839-1.856:d:6)
(4) Elemental Analysis (Metal Analysis: ICP-AES)
  Nickel content: 16.2 mass % (theoretical value 16.0 mass %)
  CHN analysis: C, 59.3%; (theoretical value 58.9%), H, 10.2%; (theoretical value 9.9%), N, 15.9%; (theoretical value 15.3%).

Example 7: Manufacture of Compound No. 39

10.0 g (0.080 mol) of manganese (II) chloride and 49.5 g of tetrahydrofuran were loaded into a 500 ml 4-necked flask, and stirred at room temperature. A solution prepared from 11.1 g (0.080 mol) of N,N'-diisopropyl-1,4-diaza-1,3-butadiene and 54.6 g of tetrahydrofuran was added dropwise to this under ice cooling. Next, a solution prepared from 13.4 g (0.080 mol) of N,N'-di-tert-butyl-1,4-diaza-1,3-butadiene, 79.2 g of tetrahydrofuran and 1.10 g (0.16 mol) of Li was added dropwise, and after dropping the mixture was returned to room temperature and stirred for 15 hours. The solvent was removed at a bath temperature of 90° C. under slightly reduced pressure, solvent substitution was performed with n-hexane, and the mixture was filtered. The solvent was removed from the resulting filtrate, and the residue was distilled at a bath temperature of 128° C., a pressure of 60 Pa and a column top temperature of 118° C. to obtain the target substance as a black solid. The yield was 12.8 g, and the percentage yield was 44%.

(Analysis Values)
(1) Normal Pressure TG-DTA
  50% mass reduction temperature: 219° C. (Ar flow: 100 ml/min, temperature rise 10° C./min, sample volume: 9.805 mg)
(2) Reduced Pressure TG-DTA
  50% mass reduction temperature: 140° C. (10 Torr, Ar flow: 50 ml/min, temperature rise 10° C./min, sample volume: 9.847 mg)
(3) Elemental Analysis (Metal Analysis: ICP-AES)
  Manganese content: 15.5 mass % (theoretical value 15.1 mass %)
  CHN analysis: C, 60.3%; (theoretical value 59.5%), H, 10.2%; (theoretical value 10.0%), N, 15.2%; (theoretical value 15.4%).

[Evaluation Example 1] Physical Properties Evaluation of Cobalt Compounds

The states of the Compounds Nos. 2, 3, 5, 6 and 9 and the Comparative Compound 1 shown below at normal pressure, 30° C. were each visually observed, and the melting points of the solid compounds were measured with a micro-melting point measurement apparatus. The temperatures at which thermal decomposition began with the Compounds Nos. 2, 3, 5, 6 and 9 and the Comparative Compound 1 shown below were measured by differential scanning calorimetry (DSC). The temperatures at which the weights of the Compounds Nos. 2, 3, 5, 6 and 9 and the Comparative Compound 1 shown below were reduced by 50% were measured by TG-DTA. The results are shown in Table 1. TD-GTA measurement conditions: 10 Torr, Ar flow: 50 ml/min, temperature rise 10° C./min, sample volume about 10 mg

[Chemical Formula 15]

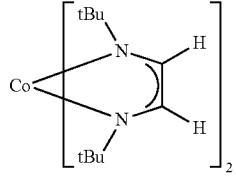

Comp. Compound No. 1

TABLE 1

| Compound | State | Melting point (° C.) | Thermal decomposition start temperature (° C.) | TG-DTA 50% mass reduction temperature (° C.) |
|---|---|---|---|---|
| Comparative Example 1 | Comparative Compound 1 | Solid | 171 | 295 | 160 |
| Evaluation Example 1-1 | Compound No. 2 | Liquid | — | 260 | 140 |
| Evaluation Example 1-2 | Compound No. 3 | Solid | <100 | 260 | 140 |
| Evaluation Example 1-3 | Compound No. 5 | Liquid | — | 260 | 150 |
| Evaluation Example 1-4 | Compound No. 6 | Solid | <100 | 260 | 140 |
| Evaluation Example 1-5 | Compound No. 9 | Liquid | — | 230 | 140 |

It can be seen from Table 1 above that while the Comparative Example 1 is a compound with a melting point of 171° C., the Evaluation Examples 1-1 to 1-5 are all compounds that are liquid under conditions of normal pressure, 100° C. Since a thin film-forming material with a low melting point is easy to transport, productivity can be improved with such a thin film-forming material. The DSC results show that the Evaluation Examples 1-1 to 1-5 begin thermal decomposition at lower temperatures than Comparative Example 1. The TG-DTA results show that Evaluation Examples 1-1 to 1-5 have lower 50% mass reduction temperatures than Comparative Example 1. This shows that Comparative Examples 1-1 to 1-5 exhibit better vapor pressure than Comparative Example 1.

[Evaluation Example 2] Physical Properties Evaluation of Nickel Compounds

The states of Compound No. 30 and Comparative Compound 2 shown below at normal pressure, 30° C. were each visually observed, and the melting points of the solid compounds were measured with a micro-melting point measurement apparatus. The temperatures at which thermal decomposition began with the Compound No. 30 and the Comparative Compound 2 shown below were measured by DSC. The results are shown in Table 2.

[Chemical Formula 16]

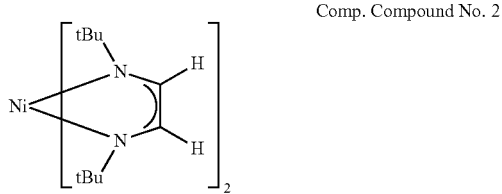

TABLE 2

| | Compound | State | Melting point (° C.) | Thermal decomposition start temperature (° C.) |
|---|---|---|---|---|
| Comparative Example 2 | Comparative Compound 2 | Solid | 185 | 220 |
| Evaluation Example 2-1 | Compound No. 30 | Solid | <100 | 210 |

It can be seen from Table 2 that while the Comparative Example 2 is a compound with a melting point of 185° C., the Evaluation Example 2-1 is a compound that is liquid under conditions of normal pressure, 100° C. Since a thin film-forming material with a low melting point is easy to transport, productivity can be improved with such a thin film-forming material. The DSC results show that Evaluation Example 2-1 begins thermal decomposition at a lower temperature than Comparative Example 2.

[Evaluation Example 3] Physical Properties Evaluation of Manganese Compounds

The states of Compound No. 39 and Comparative Compound 3 shown below at normal pressure, 30° C. were each observed with the naked eye, and the melting points of the solid compounds were measured with a micro-melting point measurement apparatus. The temperatures at which thermal decomposition began with the Compound No. 39 and the Comparative Compound 3 shown below were measured by DSC. The results are shown in Table 3.

[Chemical Formula 17]

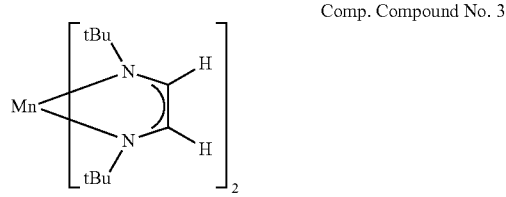

TABLE 3

| | Compound | State | Melting point (° C.) | Thermal decomposition start temperature (° C.) |
|---|---|---|---|---|
| Comparative Example 3 | Comparative Compound 3 | Solid | 155 | 325 |
| Evaluation Example 3-1 | Compound No. 39 | Solid | <100 | 230 |

It can be seen from Table 1 that that while the Comparative Example 3 is a compound with a melting point of 155° C., the Evaluation Example 3-1 is a compound that is liquid under conditions of normal pressure, 100° C. Since a thin film-forming material with a low melting point is easy to transport, productivity can be improved with such a thin film-forming material. The DSC results show that Evaluation Example 3-1 begins thermal decomposition at a much lower temperature than Comparative Example 3.

[Example 8] Manufacture of Metal Cobalt Thin Films by ALD

Metal cobalt thin films were manufactured on Cu substrates by ALD under the following conditions using the Compounds Nos. 2, 3, 5, 6 and 9 as materials for chemical vapor deposition, using the ALD apparatus shown in FIG. 1. When the film thicknesses of the resulting thin films were measured by the X-ray reflectivity method and the thin film structures and compositions were confirmed by X-ray analysis and X-ray photoelectron spectroscopy (XPS analysis), the film thicknesses were 3 to 6 nm, the films were composed of metal cobalt (confirmed from Co2p peak in XPS analysis), and the carbon contents were below the detection limit of 0.1 atom %. The film thickness obtained per cycle was 0.02 to 0.04 nm.

(Conditions)

Reaction temperature (substrate temperature): 270° C., reactive gas: hydrogen gas (Steps)

150 cycles were performed, with each cycle consisting of the series of steps shown in (1) to (4) below:

(1) Vapor from chemical vapor deposition material that has been vaporized at a material container heating temperature of 100° C. and a material container internal pressure of 100 Pa is introduced, and deposited for 30 seconds at a system pressure of 100 Pa;

(2) Unreacted material is removed by 5 seconds of argon purging;

(3) Reactive gas is introduced, and reacted for 30 seconds at a system pressure of 100 Pa;
(4) Unreacted material is removed by 5 seconds of argon purging.

[Comparative Manufacturing Example 1]
Manufacture of Metal Cobalt Thin Film by ALD An attempt was made to manufacture a metal cobalt thin film on a Cu substrate by the same methods as in Example 8 using Comparative Compound 1 as the material for chemical vapor deposition, but a smooth thin film could not be obtained. The carbon content of the Co-containing material formed on the Cu substrate was 10% or more.
(Conditions)
Reaction temperature (substrate temperature): 270° C., reactive gas: hydrogen gas
(Steps)
150 cycles were performed, with each cycle consisting of the series of steps shown in (1) to (4) below:
(1) Vapor from chemical vapor deposition material that has been vaporized at a material container heating temperature of 100° C. and a material container internal pressure of 100 Pa is introduced, and deposited for 30 seconds at a system pressure of 100 Pa;
(2) Unreacted material is removed by 5 seconds of argon purging;
(3) Reactive gas is introduced, and reacted for 30 seconds at a system pressure of 100 Pa;
(4) Unreacted material is removed by 5 seconds of argon purging.

The results of Example 8 show that good quality metal cobalt thin films could be obtained in all cases. In Comparative Manufacturing Example 1, on the other hand, a smooth thin film could not be formed on the Cu substrate, and small lumps appeared scattered on the substrate. Moreover, the carbon content of the Co-containing material formed on the Cu substrate was 10% or more, indicating that a good quality metal cobalt thin film could not be obtained.

[Example 9] Manufacture of Metal Nickel Thin Film by ALD

A metal nickel thin film was manufactured on a Cu substrate by ALD under the following conditions using Compound No. 30 as the material for chemical vapor deposition, using the ALD apparatus shown in FIG. 1. When the film thickness of the resulting thin film was measured by an X-ray reflectivity method and the thin film structure and composition were confirmed by X-ray analysis and X-ray photoelectron spectroscopy, the film thickness was 3 to 6 nm, the film was composed of metal nickel (confirmed from Ni2p peak in XPS analysis), and the carbon content was below the detection limit of 0.1 atom %. The film thickness obtained per cycle was 0.02 to 0.04 nm.
(Conditions)
Reaction temperature (substrate temperature): 220° C., reactive gas: hydrogen gas
(Steps)
150 cycles were performed, with each cycle consisting of the series of steps shown in (1) to (4) below:
(1) Vapor from chemical vapor deposition material that has been vaporized at a material container heating temperature of 100° C. and a material container internal pressure of 100 Pa is introduced, and deposited for 30 seconds at a system pressure of 100 Pa;
(2) Unreacted material is removed by 5 seconds of argon purging;
(3) Reactive gas is introduced, and reacted for 30 seconds at a system pressure of 100 Pa;
(4) Unreacted material is removed by 5 seconds of argon purging.

The results of Example 9 show that a good quality metal nickel thin film could be obtained at a reaction temperature below 250° C.

[Example 10] Manufacture of Metal Manganese Thin Film by ALD

A metal manganese thin film was manufactured on a Cu substrate by ALD under the following conditions with Compound No. 39 as the material for chemical vapor deposition, using the ALD apparatus shown in FIG. 1. When the film thickness of the resulting thin film was measured by the X-ray reflectivity method and the thin film structure and composition were confirmed by X-ray analysis and X-ray photoelectron spectroscopy, the film thickness was 3 to 6 nm, the film was composed of metal manganese (confirmed from the Mn2p peak in XPS analysis), and the carbon content was below the detection limit of 0.1 atom %. The film thickness obtained per cycle was 0.02 to 0.04 nm.
(Conditions)
Reaction temperature (substrate temperature): 240° C., reactive gas: hydrogen gas
(Steps)
150 cycles were performed, with each cycle consisting of the series of steps shown in (1) to (4) below:
(1) Vapor from chemical vapor deposition material that has been vaporized at a material container heating temperature of 100° C. and a material container internal pressure of 100 Pa is introduced, and deposited for 30 seconds at a system pressure of 100 Pa;
(2) Unreacted material is removed by 5 seconds of argon purging;
(3) Reactive gas is introduced, and reacted for 30 seconds at a system pressure of 100 Pa;
(4) Unreacted material is removed by 5 seconds of argon purging.

The results of Example 9 show that a good quality metal manganese thin film could be obtained at a reaction temperature below 250° C.

The invention claimed is:
1. A compound represented by the general formula (I) or (II) below:

[Chemical Formula 1]

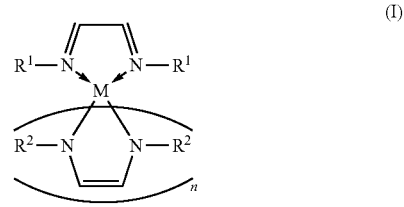

(I)

[in the formula, each of $R^1$ and $R^2$ independently represent a $C_{1\sim12}$ hydrocarbon group, and $Si(R^3)_3$ is optionally substituted for a hydrogen atom in the hydrocarbon group; however, $R^1$ and $R^2$ are different groups; $R^3$ represents a methyl or ethyl group; M represents a metal atom or silicon atom; and n is an integer from 1 to 4]

[Chemical Formula 2]

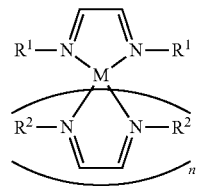

(II)

[in the formula, $R^1$, $R^2$, $R^3$, M and n are as in the general formula (I)].

2. The compound of claim 1, wherein M is copper, iron, nickel, cobalt or manganese in the general formula (I) or general formula (II).

3. The compound of claim 1, wherein n in the general formula (I) or general formula (II) is 1.

4. A thin film-forming material containing the compound of claim 1.

5. A thin film manufacturing method comprising: introducing vapor containing a compound obtained by vaporizing the thin film-forming material of claim 4, into a film-forming chamber containing a substrate; and decomposing and/or chemically reacting the compound to thereby form, on the surface of the substrate, a thin film containing at least one kind of atom selected from a metal atom and a silicon atom.

6. The compound of claim 2, wherein n in the general formula (I) or general formula (II) is 1.

7. A thin film-forming material containing the compound of claim 2.

8. A thin film-forming material containing the compound of claim 3.

9. A thin film manufacturing method comprising: introducing vapor containing a compound obtained by vaporizing the thin film-forming material of claim 7, into a film-forming chamber containing a substrate; and decomposing and/or chemically reacting the compound to thereby form, on the surface of the substrate, a thin film containing at least one kind of atom selected from a metal atom and a silicon atom.

10. A thin film manufacturing method comprising: introducing vapor containing a compound obtained by vaporizing the thin film-forming material of claim 8, into a film-forming chamber containing a substrate; and decomposing and/or chemically reacting the compound to thereby form, on the surface of the substrate, a thin film containing at least one kind of atom selected from a metal atom and a silicon atom.

* * * * *